(12) United States Patent
Liang et al.

(10) Patent No.: US 10,975,306 B2
(45) Date of Patent: Apr. 13, 2021

(54) LATERAL TRIFLUOROMETHYL-CONTAINING LIQUID CRYSTAL COMPOUND, LIQUID CRYSTAL MIXTURE AND DISPLAY DEVICE

(71) Applicant: SHIJIAZHUANG CHENGZHI YONGHUA DISPLAY MATERIAL CO., LTD, Shijiazhuang (CN)

(72) Inventors: Zhian Liang, Shijiazhuang (CN); Wei Zhang, Shijiazhuang (CN); Kai Xu, Shijiazhuang (CN); Kui Wang, Shijiazhuang (CN); Yang Xiang, Shijiazhuang (CN); Shen Yuan, Shijiazhuang (CN); Minsheng Guo, Shijiazhuang (CN); Limei Zhang, Shijiazhuang (CN)

(73) Assignee: Shijiazhuang Chengzhi Yonghua Display Material Co., Ltd., Shijiazhuang (CN)

( * ) Notice: Subject to any disclaimer, the term of this patent is extended or adjusted under 35 U.S.C. 154(b) by 9 days.

(21) Appl. No.: 16/164,149

(22) Filed: Oct. 18, 2018

(65) Prior Publication Data
US 2019/0144751 A1 May 16, 2019

(30) Foreign Application Priority Data

Nov. 16, 2017 (CN) .......................... 2017 1 1140476

(51) Int. Cl.
| | | |
|---|---|---|
| *G02F 1/1333* | (2006.01) | |
| *C09K 19/34* | (2006.01) | |
| *C09K 19/30* | (2006.01) | |
| *C09K 19/54* | (2006.01) | |
| *C07C 43/225* | (2006.01) | |
| *C07D 309/06* | (2006.01) | |
| *C07D 319/06* | (2006.01) | |
| *C09K 19/04* | (2006.01) | |
| *C09K 19/12* | (2006.01) | |

(52) U.S. Cl.
CPC ........ *C09K 19/3491* (2013.01); *C07C 43/225* (2013.01); *C07D 309/06* (2013.01); *C07D 319/06* (2013.01); *C09K 19/0403* (2013.01); *C09K 19/3003* (2013.01); *C09K 19/3066* (2013.01); *C09K 19/3402* (2013.01); *C09K 19/3405* (2013.01); *C09K 19/542* (2013.01); *C07C 2601/02* (2017.05); *C07C 2601/08* (2017.05); *C07C 2601/14* (2017.05); *C09K 2019/0448* (2013.01); *C09K 2019/0466* (2013.01); *C09K 2019/122* (2013.01); *C09K 2019/123* (2013.01); *C09K 2019/124* (2013.01); *C09K 2019/301* (2013.01); *C09K 2019/3004* (2013.01); *C09K 2019/3009* (2013.01); *C09K 2019/3016* (2013.01); *C09K 2019/3019* (2013.01); *C09K 2019/3025* (2013.01); *C09K 2019/3408* (2013.01); *C09K 2019/3422* (2013.01); *C09K 2019/3425* (2013.01); *C09K 2019/548* (2013.01)

(58) Field of Classification Search
CPC ............ C09K 19/3491; C09K 19/0403; C09K 19/3003; C09K 19/3066; C09K 19/3402; C09K 19/3405; C09K 19/542; C09K 2019/0488; C09K 2019/0466; C09K 2019/122; C09K 2019/123; C09K 2019/124; C09K 2019/3004; C09K 2019/3009; C09K 2019/301; C09K 2019/3016; C09K 2019/3019; C09K 2019/3025; C09K 2019/3408; C09K 2019/3422; C09K 2019/3425; C09K 2019/548; G02F 1/1333; C07C 43/225; C07C 2601/02; C07C 2601/14; C07C 2601/08; C07D 309/06; C07D 319/06
USPC ..................................................... 252/299.61
See application file for complete search history.

(56) References Cited

FOREIGN PATENT DOCUMENTS

DE          43 36 265 A1 * 10/1993 ............. C09K 19/20

\* cited by examiner

*Primary Examiner* — Geraldina Visconti
(74) *Attorney, Agent, or Firm* — Muncy, Geissler, Olds & Lowe, P.C.

(57) ABSTRACT

Provide are a liquid crystal compound represented by formula I, and a liquid crystal mixture comprising the compound

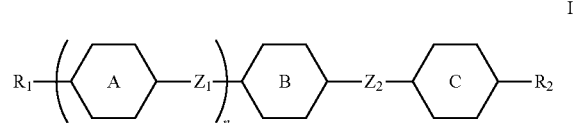

A lateral trifluoromethyl-containing liquid crystal compound having the structural characteristics of Formula I not only has a negative dielectric anisotropy (Δε), an appropriate optical anisotropy (Δn), a higher clearing point (CP), a prominent low-temperature miscibility with other liquid crystals, and a low rotary viscosity (γ1), but also has a good stability to UV and high temperatures, particularly, a negative dielectric anisotropy. Same can be applied to the formulation of liquid crystal compositions of positive and negative types, and it is particularly prominent that same has the advantages of a good solubility at low temperatures and a high transmittance.

9 Claims, 1 Drawing Sheet

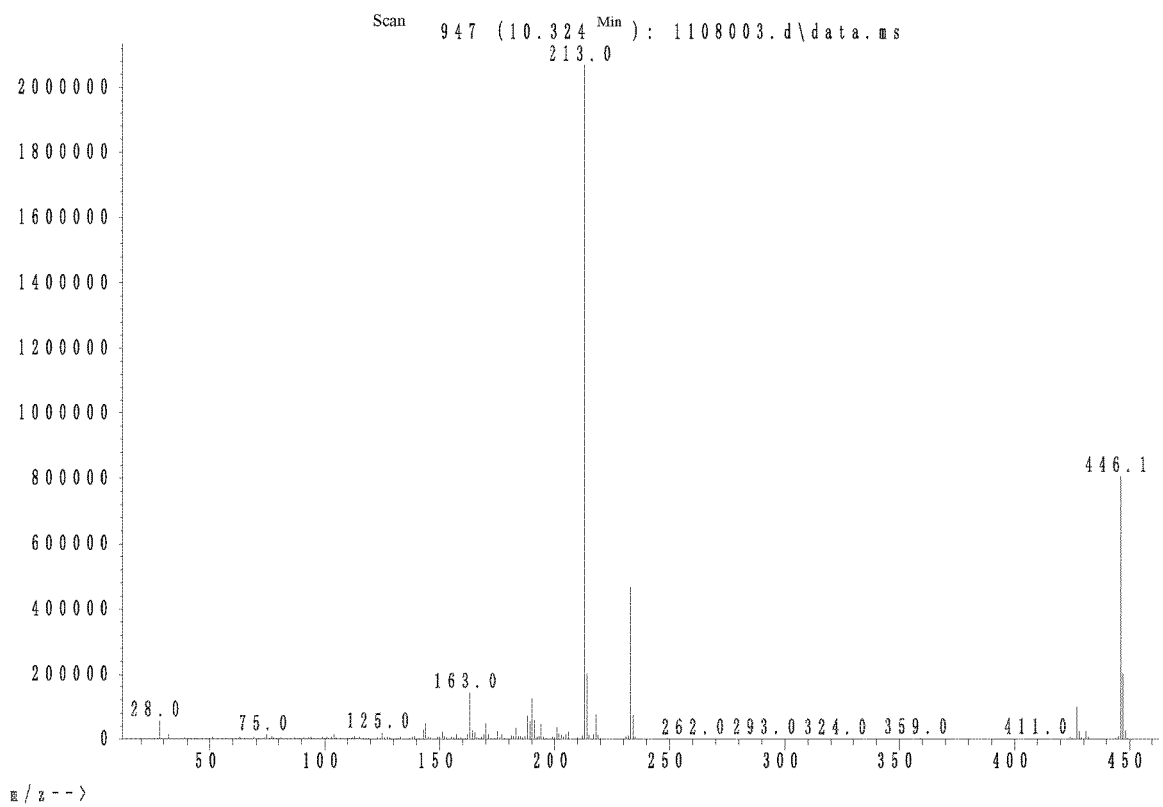

LATERAL TRIFLUOROMETHYL-CONTAINING LIQUID CRYSTAL COMPOUND, LIQUID CRYSTAL MIXTURE AND DISPLAY DEVICE

TECHNICAL FIELD

The present invention belongs to the field of liquid crystal compounds and applications thereof, and particularly relates to a lateral trifluoromethyl-containing liquid crystal compound, a liquid crystal mixture, and a liquid crystal display device using such a compound or mixture.

BACKGROUND ART

Since the Austrian scientist Reinitzer first synthesized a liquid crystal in 1888, the actual development of the liquid crystal industry is in the recent more than 30 years; since liquid crystal display materials have obvious advantages, such as a low drive voltage, a small power consumption, high reliability, a great display information amount, color display, no flicker, a capability of achieving panel display, etc., both liquid crystal monomers and liquid crystal displays have gone through a huge development, and liquid crystal monomers have been used in the synthesis of more than 10,000 kinds of liquid crystal materials, wherein there are thousands of common liquid crystal display materials, and by the classification according to the characteristics of the central bridge bond and rings of liquid crystal molecules, there are mainly biphenyl liquid crystals, phenyl cyclohexane liquid crystals, ester liquid crystals, alkynes, difluoromethoxy bridge types, ethane types and heterocyclic types. The liquid crystal display is also developed from TN and STN of black and white small screen in 30 years ago to the current TN-TFT, VA-TFT, IPS-TFT, PDLC of scale color screen, etc.

Main new liquid crystal display modes include optical compensation bending mode (OCB), coplanar transformation liquid crystal display (IPS), vertical alignment mode (VA), axisymmetric microstructure liquid crystal display (ASM), multi-domain twisted liquid crystal display, etc.

In the various display modes, liquid crystal cells have different designs and different driving methods, and the orientations of liquid crystal molecular directors with respect to glass substrates are different, wherein in the optical compensation bending mode (OCB) and the coplanar transformation liquid crystal display (IPS), liquid crystal molecular directors are parallel to the direction of the glass substrates, while in the vertical alignment mode (VA) and the axisymmetric microstructure liquid crystal display (ASM), the liquid crystal molecular directors are perpendicular to the direction of the glass substrates in the absence of an electric field.

With regard to the IPS of the parallel arranged mode, the dielectric anisotropy (Δε) of the liquid crystal may be either positive or negative.

In the vertical alignment mode (VA), all liquid crystal molecules in a null field are perpendicular to the direction of the glass substrates and parallel to a vertical incident light. When a polarizer is orthogonal, a good dark state is shown; therefore this kind of device has a good contrast, and the dielectric anisotropy (Δε) of the liquid crystal used has to be negative. The optical anisotropy (Δε) of the crystal, the thickness (d) of the liquid crystal cell and the wavelength (λ) of the incident light barely affect the contrast. The response time of the vertical alignment mode (VA) is much shorter than that of a twist-type device and is about half of that.

Under the influence of an applied voltage, a VA device mainly produces a bending deformation of liquid crystal molecules, ECB produces a splay deformation of liquid crystal molecules, and the twisted display produces a twist deformation of liquid crystal molecules; the response times thereof are also inversely proportional to bending, splay, and twist elastic constants, respectively, because in general cases for most liquid crystals, the bending elastic constant of liquid crystal is greater than the splay elastic constant and the splay elastic constant is greater than the twist elastic constant, which is also the reason why the VA device has a faster response time.

In order to enable the performance of a display device to be closer to ideal, people have always been working to study new liquid crystal compounds, which allows the performances of liquid crystal compounds and display devices to continuously advance.

In fact, in many cases, liquid crystal mixtures can also work at a very low temperature, especially in an outdoor environment, and liquid crystals are required to have a good low temperature performance to investigate that liquid crystals can also work at −30° C. for a long time; that is to say, during the storage of the liquid crystal monomer at a low temperature for a long time, no monomer is precipitated, so it is still necessary to develop a liquid crystal having a good miscibility at a low temperature.

Liquid crystal display devices are increasingly oriented toward high pixel density designs, and for the control of backlight power consumption, the requirements for the light transmittance of the liquid crystal layer are also getting higher and higher, so to develop a liquid crystal with a high transmittance is an important direction for the development of liquid crystals currently.

SUMMARY OF THE INVENTION

Surprisingly, a lateral trifluoromethyl-containing liquid crystal compound having the structural characteristics of Formula I not only has a negative dielectric anisotropy (Δε), an appropriate optical anisotropy (Δn), a higher clearing point (CP), a prominent low-temperature miscibility with other liquid crystals, and a low rotary viscosity (γ1), but also has a good stability to UV and high temperatures, particularly, a negative dielectric anisotropy. Same can be applied to the formulation of liquid crystal compositions of positive and negative types, and it is particularly prominent that same has the advantages of a good solubility at low temperatures and a high transmittance.

The present invention specifically provides a liquid crystal compound represented by formula I:

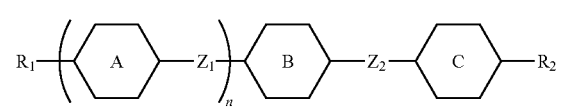

I wherein $R_1$ and $R_2$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

n represents 1 or 2;

$Z_1$ represents one or more of a single bond, —$CF_2O$—, —$OCF_2$—, —COO—, —C≡C— and/or —$CH_2O$—;

$Z_2$ represents —$CF_2O$—, —$OCF_2$—, —$CH_2O$— or —$OCH_2$—; and

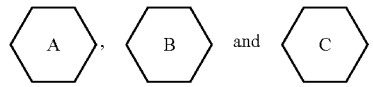

each independently represent one or more of phenylene, phenylene substituted with one or more fluorines and/or one trifluoromethyl, cyclohexenylene, cyclohexylene, or groups formed by substituting one or two non-connected $CH_2$ in cyclohexylene with O, with one of said

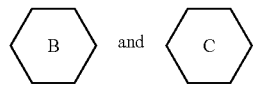

representing phenylene substituted with one trifluoromethyl, wherein said phenylene substituted with one trifluoromethyl may be substituted with fluorine.

The compound represented by formula I is preferably a compound represented by formula Ia, Ib, Ic or Id:

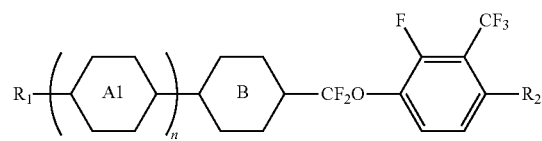

Ia

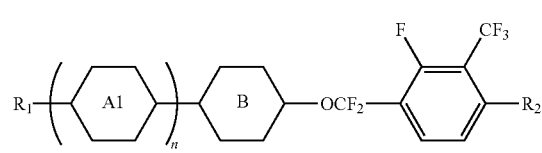

Ib

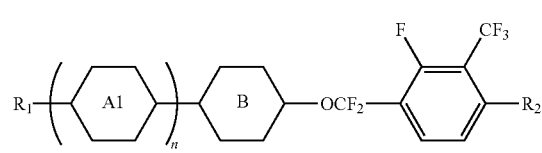

Ic

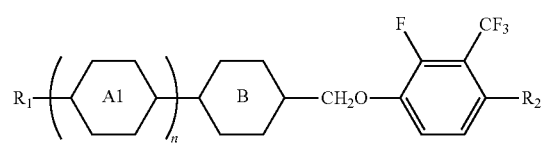

Id

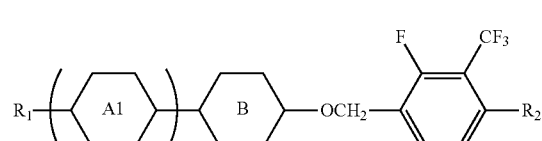

Ie

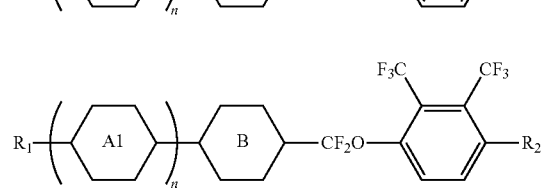

-continued

If

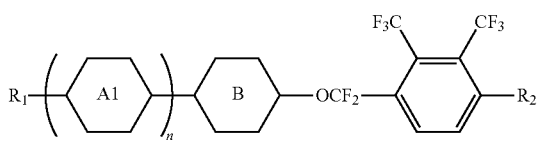

Ig

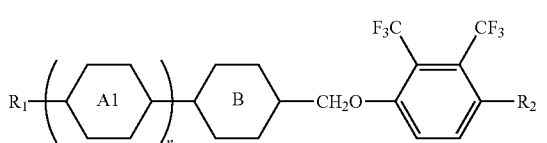

Ih

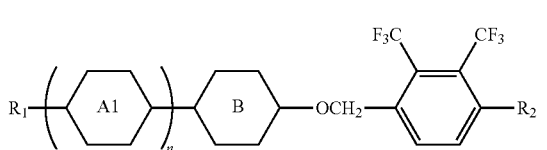

wherein $R_1$ and $R_2$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

represents one or more of

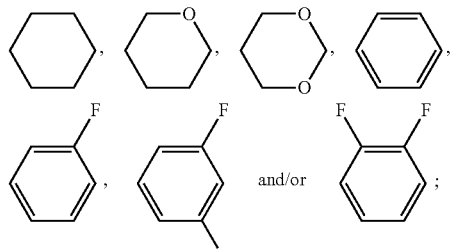

and n represents 1 or 2.

A pure compound of formula I is colourless, and has different properties depending on $R_1$, $R_2$,

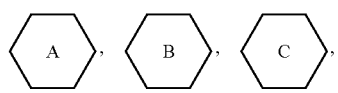

n, $Z_1$ and $Z_2$. It may be used for the formulation of a positive liquid crystal mixture, and may also be used for the formulation of a negative liquid crystal mixture for use in display devices of various modes such as OCB, TN, STN, IPS, FFS and VA, and therefore it has a wider range of applications.

It may also be used as a base material for liquid crystal mixtures, and may also be added, as an additive material, into liquid crystal base materials composed of other types of compounds, for example, to improve the low temperature solubility and/or the vertical dielectricity, dielectric anisotropy $\Delta\varepsilon$ and/or rotary viscosity $\gamma_1$ and/or threshold voltage $V_{th}$ and/or contrast at a low temperature and/or optical anisotropy $\Delta n$ and/or clearing point Cp of the liquid crystal mixture, and it is particularly prominent that it has the advantages of a good solubility at low temperatures and a high transmittance.

The compound represented by formula I is further preferably a compound represented by formula I1 to I34:

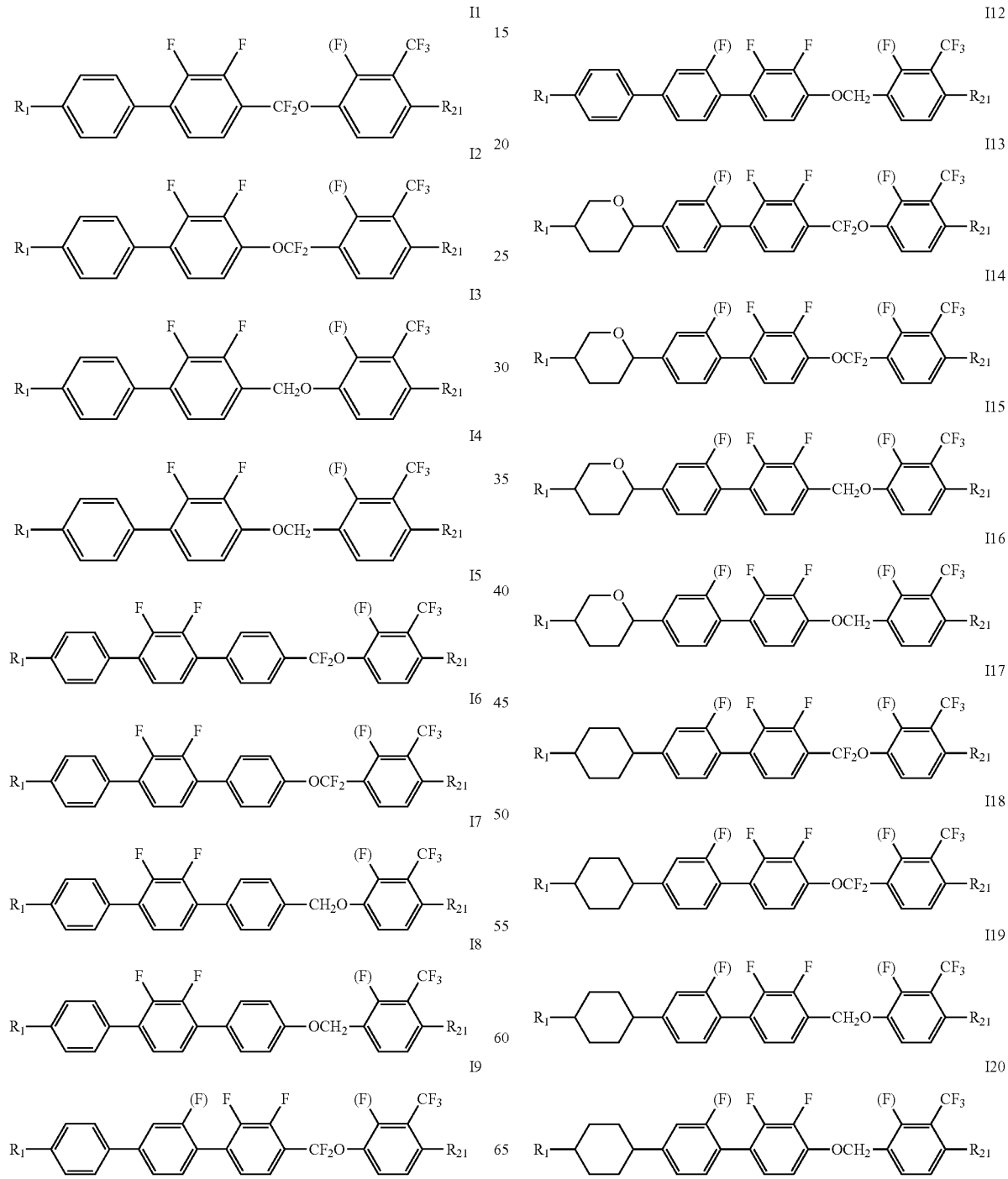

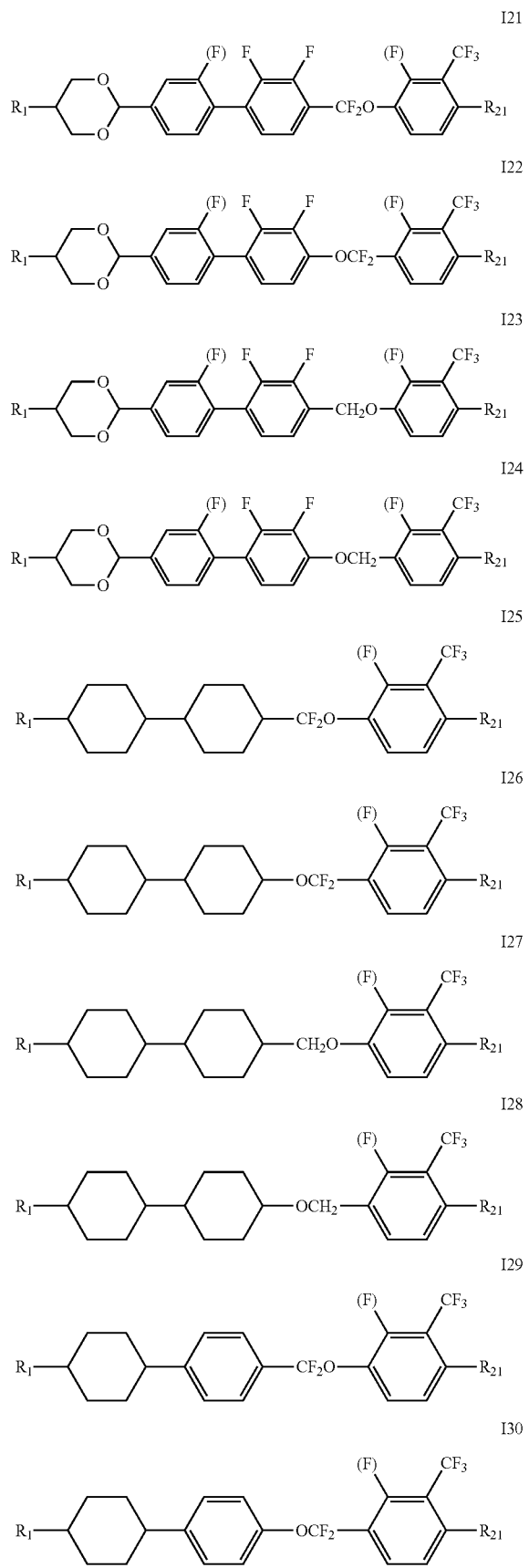

wherein each $R_1$ independently represents H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

each (F) independently represents F or H; and each $R_{21}$ independently represents H, an alkyl group having a carbon atom number of 1-5, an alkenyl group having a carbon atom number of 2-6, or an alkoxy group having a carbon atom number of 1-5.

The lateral trifluoromethyl-containing compounds of general formulas I1 to I32 have a particularly prominently larger vertical dielectricity ($\varepsilon_\perp$), an appropriate optical anisotropy ($\Delta n$), a good low-temperature miscibility with other liquid crystals, and a low rotary viscosity, and also has a good stability to ultraviolet light and high temperatures.

With regard to the lateral trifluoromethyl-containing compounds of general formulas I1 to I32, depending on the respective groups, liquid crystal molecules of different structures have different degrees of conjugation, the optical anisotropies ($\Delta n$) thereof can achieve values within a range between 0.05 and 0.35; the numbers of rings are different, the substituents are different, and the clearing points can achieve a range of 20–200° C.; in addition to the above-mentioned characteristics, the compounds of general formulas I1 to I32 further have a good low-temperature miscibility with other liquid crystals, and can improve the low-temperature characteristics of mixed liquid crystals. The structure of the lateral trifluoromethyl group together with the $Z_2$ linking group brings about the characteristics of improved low temperature properties, increased vertical dielectricity, and maintained low viscosity.

The present invention further provides a liquid crystal mixture comprising one or more compounds represented by formula I and one or more compounds represented by formula II

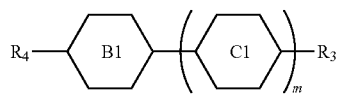

II wherein $R_3$ and $R_4$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

m represents 1 or 2; and

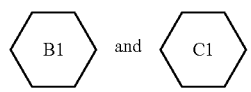

each independently represent one or more of phenylene, cyclohexylene and/or cyclohexenylene.

The concentrations (in mass percentage, the same hereinafter) of said compound represented by formula I and said compound represented by formula II comprised in the mixture are respectively 1-40% and 1-65%, preferably; and it is further preferable that the concentrations of said compound represented by formula I and said compound represented by formula II are respectively 2-30% and 15-55%.

The optimum concentration of the compound represented by formula I is 5-25%, and the optimum concentration of the compound represented by formula II is 25-40%;

said one or more compounds represented by formula II are preferably one or more of compounds represented by formulas II1 to II22 below:

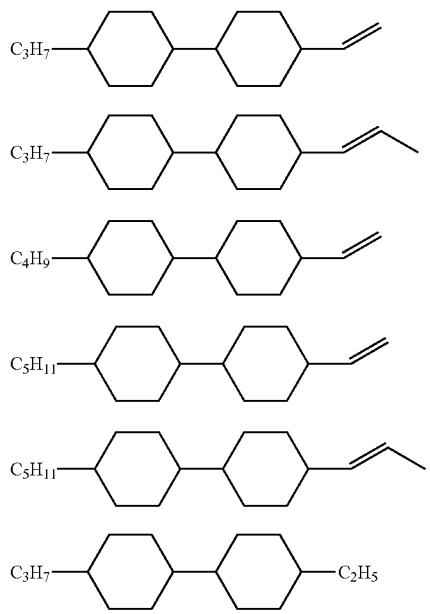

II1

II2

II3

II4

II5

II6

-continued

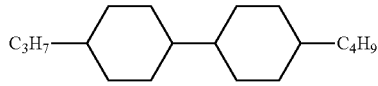
II7

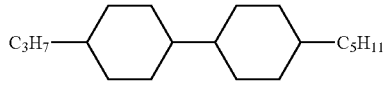
II8

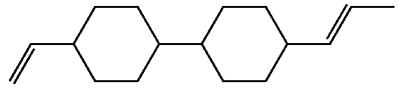
II9

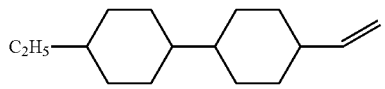
II10

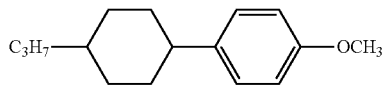
II11

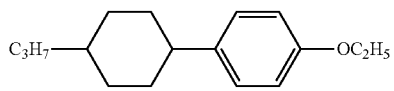
II12

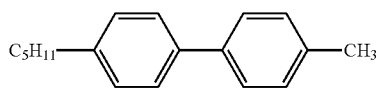
II13

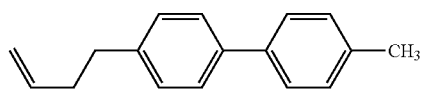
II14

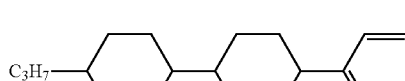
II15

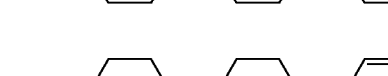
II16

II17

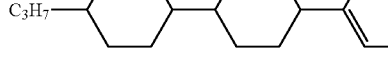
II18

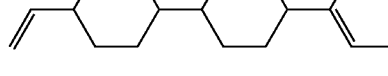
II19

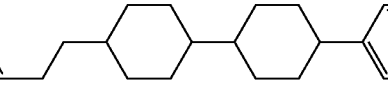
II20

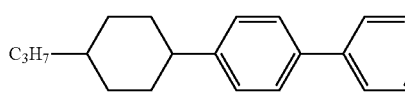
II21

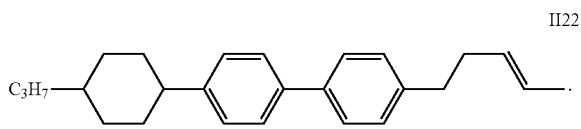

The liquid crystal composition of the present invention further comprises one or more of compounds represented by formulas III1 to III14 below:

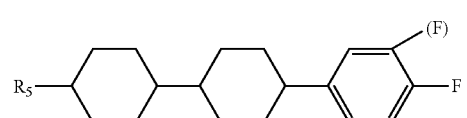
III1

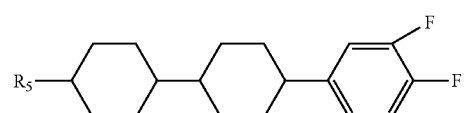
III2

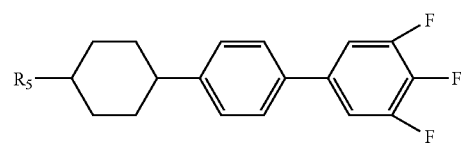
III3

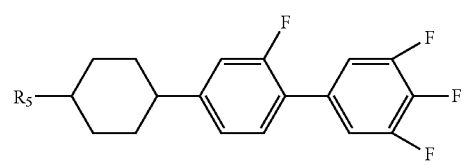
III4

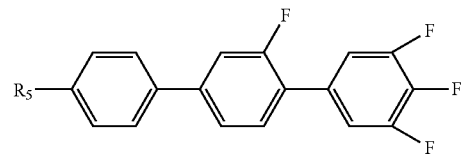
III5

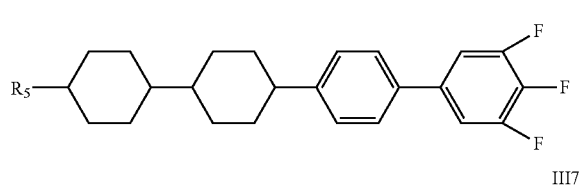
III6

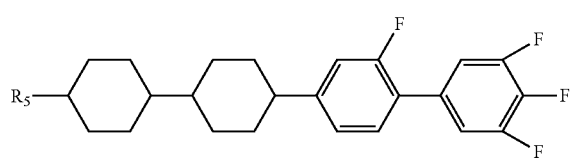
III7

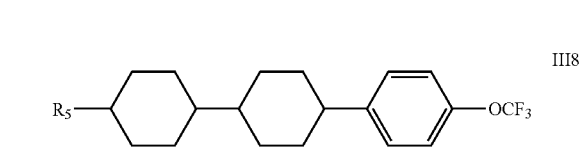
III8

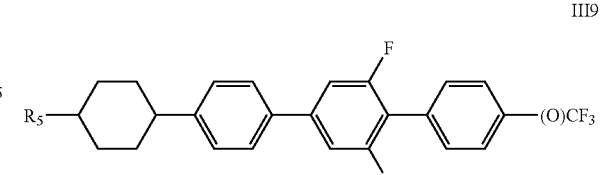
III9

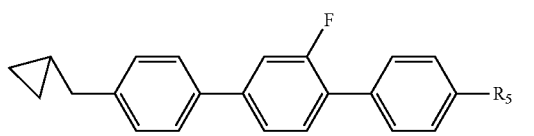
III10

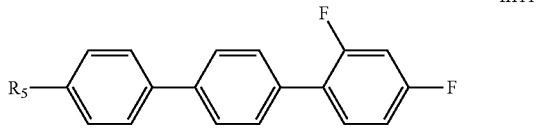
III11

III12

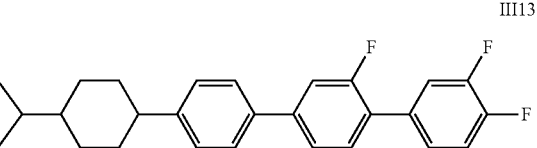
III13

III14

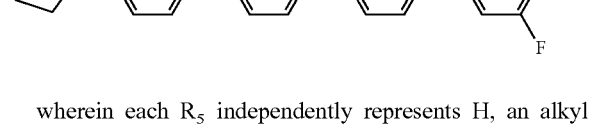

wherein each $R_5$ independently represents H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

(F) represents F or H; and (O) represents O or a single bond.

The liquid crystal composition of the present invention may further comprise one or more compounds represented by formula IV:

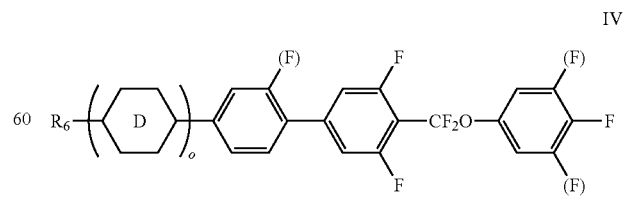
IV wherein $R_6$ represents H, an alkyl group having a carbon atom number of 1-5, an alkenyl group having a carbon atom number of 2-6, or an alkoxy group having a carbon atom number of 1-5, wherein any CH$_2$ therein may be substituted with cyclopentyl, cyclobutyl or cyclopropyl;

o represents 0 or 1;

each (F) independently represents H or F; and

represents phenylene, cyclohexylene, cyclohexenylene, or a group formed by substituting one or two non-connected CH$_2$ in cyclohexylene with O.

The compound represented by formula IV is preferably

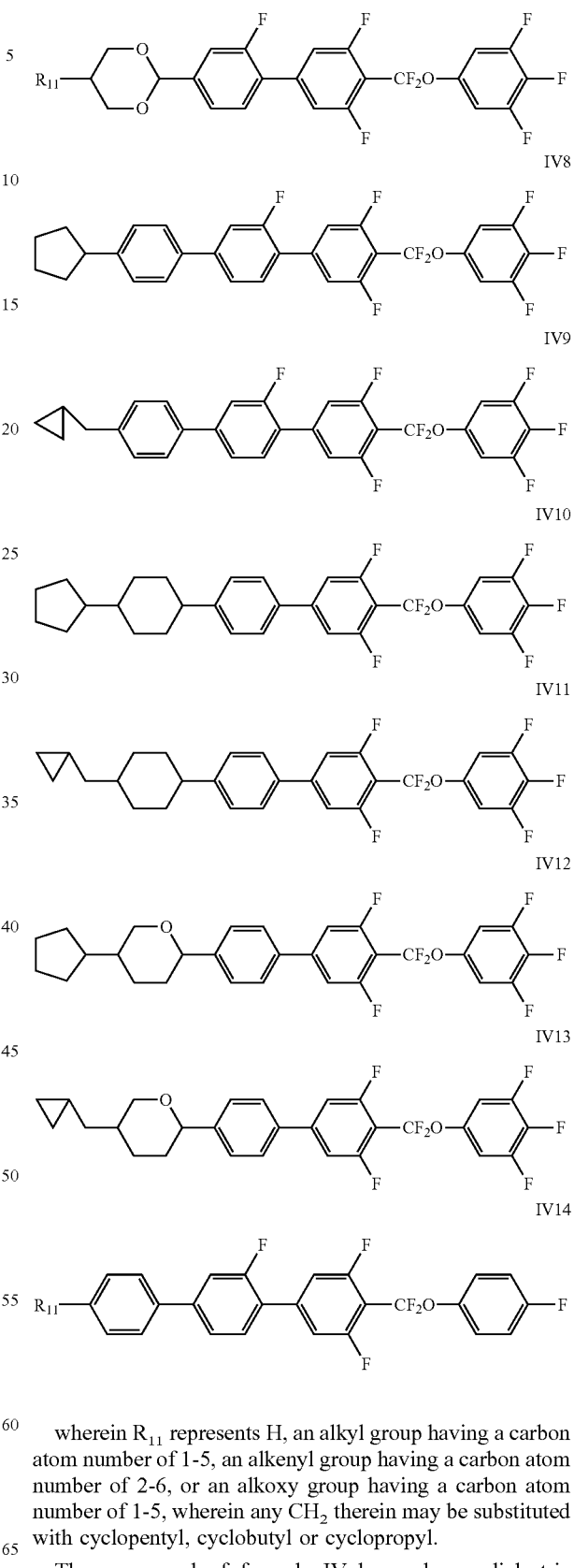

wherein R$_{11}$ represents H, an alkyl group having a carbon atom number of 1-5, an alkenyl group having a carbon atom number of 2-6, or an alkoxy group having a carbon atom number of 1-5, wherein any CH$_2$ therein may be substituted with cyclopentyl, cyclobutyl or cyclopropyl.

The compound of formula IV has a larger dielectric anisotropy and can be used for adjusting drive voltages.

To the liquid crystal composition of the present invention, a negative liquid crystal or nearly negative liquid crystal component may be further added: one or more negative compounds of formula V,

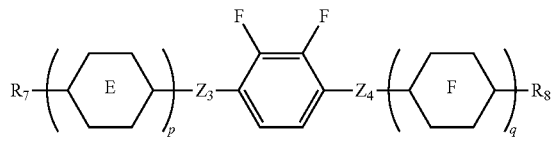
V wherein $R_7$ and $R_8$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

p and q each independently represent 0, 1 or 2, with $1 \leq p+q \leq 3$;

$Z_3$ and $Z_4$ each independently represent a single bond, —$CH_2CH_2$—, —$CH_2O$—, —$OCH_2$— or —$CF_2O$—; and

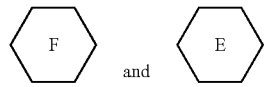

each independently represent one or more of

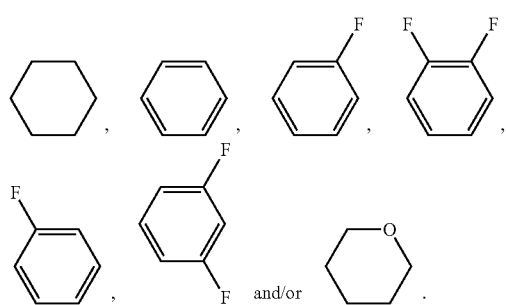
and/or

The compound represented by formula V is preferably

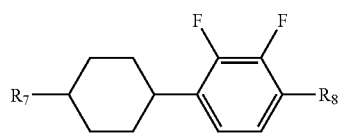
V1

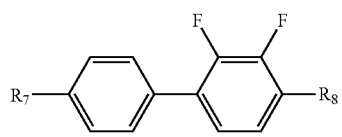
V2

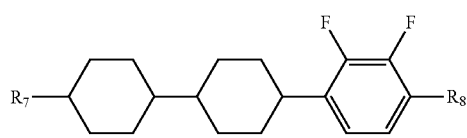
V3

-continued

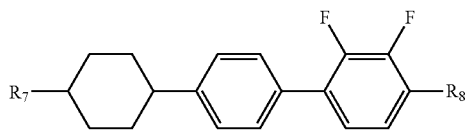
V4

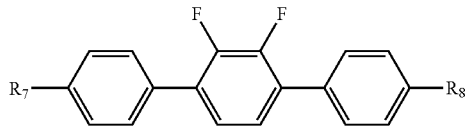
V5

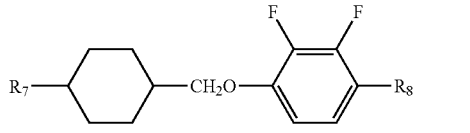
V6

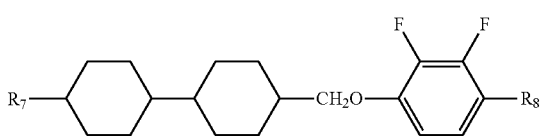
V7

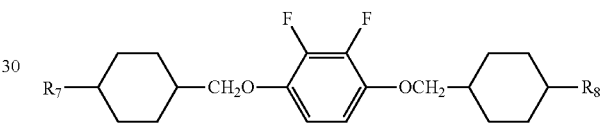
V8

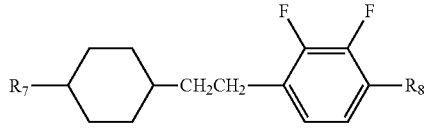
V9

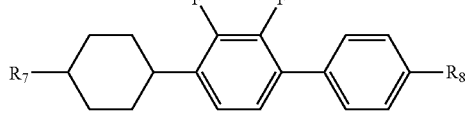
V10

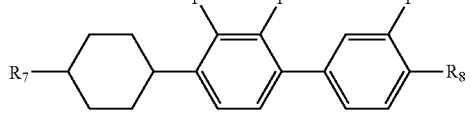
V11

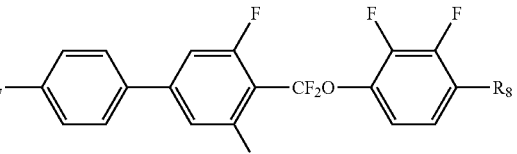
V12

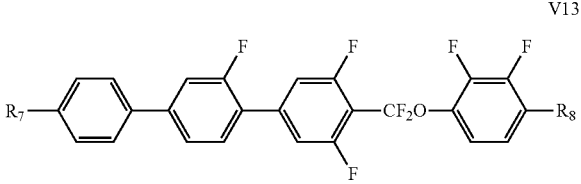
V13

-continued

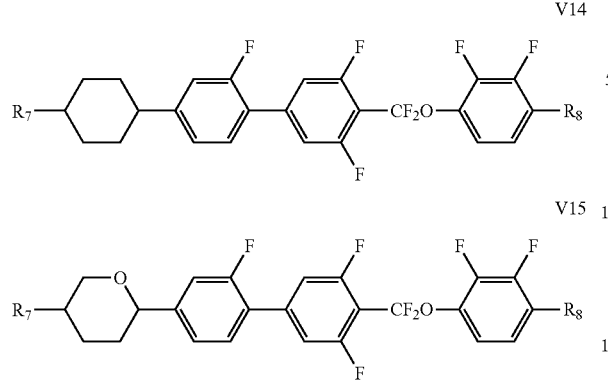

In addition, it may also be used together with the following large negative dielectricity monomers:

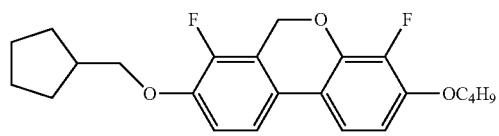

To the liquid crystal composition of the present invention, one or more compounds represented by formula VI may be further added:

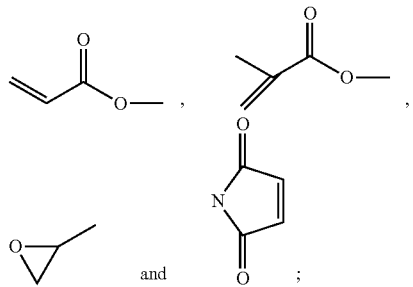

wherein each P independently represents a polymerizable functional group;
each Sp independently represents a spacer group;
M represents H, -Sp-P, F, an alkyl group having a carbon atom number of 1-5, an alkoxy group having a carbon atom number of 1-5, or an alkenyl group having a carbon atom number of 2-5;
r represents 0, 1 or 2;
$Z_5$ represents a single bond, —COO—, —C≡C—, —C=C— or —CH$_2$O—; and

each independently represent one or more of a benzene ring, cyclohexane, indane or a naphthalene ring.

The polymerizable functional group may be one of O-,

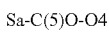

the spacer group may be an alkylene group having a carbon atom number of 1-6; and
the polymerizable compound of formula VI may be the following polymerizable compound:

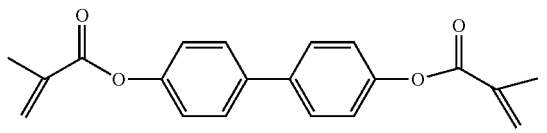

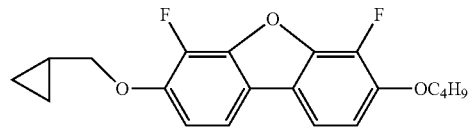

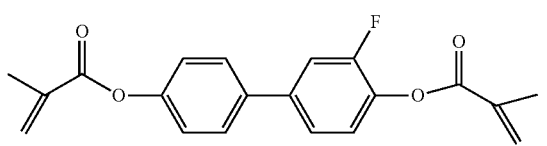

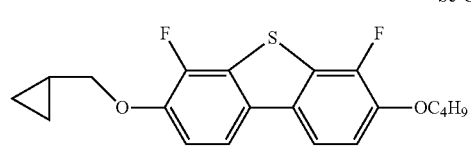

The liquid crystal composition of the invention is formulated from a plurality of compounds, generally by mixing 5-20 liquid crystal monomers, each of which monomers has a different function in the mixture system due to having a different performance parameter, so a formulation engineer would be able to adjust the various performance parameters, such as dielectric anisotropy ($\Delta\varepsilon$), optical anisotropy ($\Delta n$), nematic phase temperature range (crystallization point, clearing point CP), low rotary viscosity ($\gamma_1$), elastic constant (K), low temperature performance and transmittance, of the mixed liquid crystals by selecting various preferred monomers and optimizing the ratio of these monomers, so as to meet the requirements of display devices and adapt the matching of the PI and sealant used in the display devices, etc., thereby avoiding some display defects.

The liquid crystal mixture involved in the present invention has a wider range of dielectric anisotropy ($\Delta\varepsilon$) that can achieve a value between −5 and −2, an appropriate optical anisotropy ($\Delta n$) that can achieve a value between 0.060 and 0.300, a good low-temperature miscibility, a low rotary viscosity ($\gamma_1$) of 150 mPa·s or less, or even up to 60 mPa·s, and a higher clearing point (CP) that can achieve a value between 60° C. and 120° C., and further has a good stability to UV and high temperatures, so it can be applied to various display modes and can meet the requirements for the properties, such as different cell thickness, fast response, different drive voltage and low viscosity, of liquid crystals of various display modes.

The present invention relates not only to a liquid crystal composition comprising a liquid crystal compound of general formula I, but also to a liquid crystal display device comprising such a liquid crystal composition. Said display is an IPS display, an FFS display, a TN display, or a VA display.

To the liquid crystal composition of the present invention, a left-handed or right-handed chiral dopant may be further added to form a chiral nematic phase.

The liquid crystal or a trace amount of impurities therein easily form an excited state or even radicals after being exposed to high temperatures or irradiated with ultraviolet light or visible light, and the excited state or radicals are active in chemical properties, and may undergo chemical reactions such as oxidation which causes a decrease in the quality of the liquid crystal; During the synthesis and use of the liquid crystal compound of the present invention, various functional dopants may be further added to improve the stability of the liquid crystal, improve the quality and extend the service time of a mixed liquid crystal, wherein the contents of these dopants are preferably between 0.01% and 1%, and these dopants are mainly antioxidants, UV absorbers, and light stabilizers.

Preferred antioxidants, UV absorbers, and light stabilizers are

UV-P,

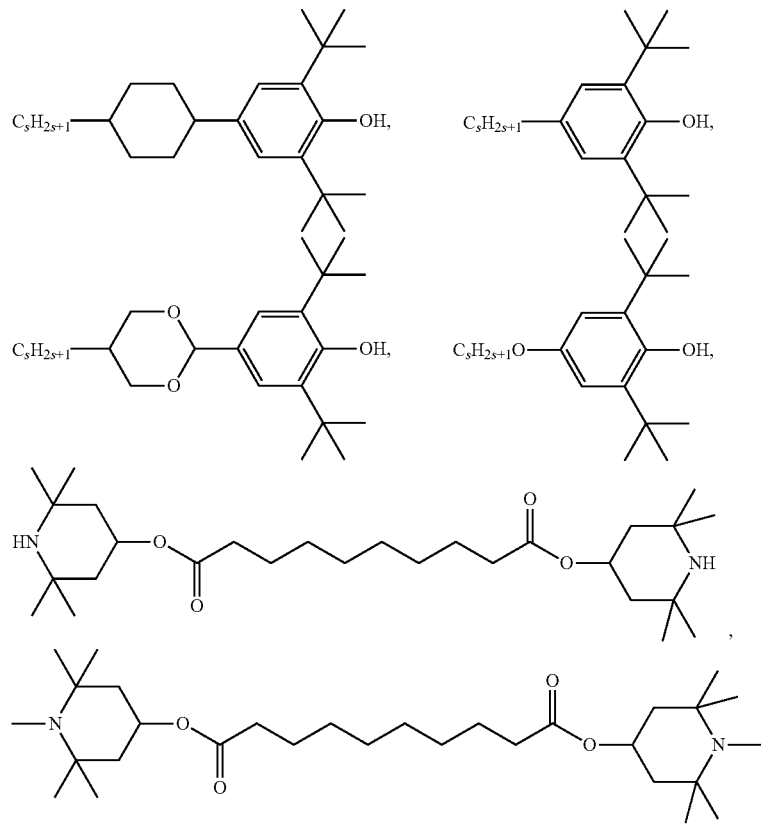

with s representing an integer of 1-10.

BRIEF DESCRIPTION OF THE DRAWINGS

The sole FIGURE is a mass spectrum of compound (1-a).

DETAILED DESCRIPTION OF EMBODIMENTS

The present invention is further described in conjunction with particular examples below, but is not limited to these examples below Said methods are all conventional methods, unless otherwise specified. Said raw materials are commercially available, unless otherwise specified.

The specific meanings of symbols in the examples and the test conditions are as follows:

Cp: represents a clearing point of a liquid crystal, with a unit of ° C.

S-N: represents a melting point of a liquid crystal from a crystal state to a nematic phase, with a unit of ° c.

$\Delta n$: represents an optical anisotropy, with $\Delta n = n_o - n_e$, in which $n_o$ is the refractive index of an ordinary light, and $n_e$ is the refractive index of an extraordinary light, with the test conditions being: 589 nm, 25±0.5° C.

$\Delta \varepsilon$: is a dielectric anisotropy, with $\Delta \varepsilon = \varepsilon// - \varepsilon \perp$, in which $\varepsilon//$ is a dielectric constant parallel to the molecular axis, and $\varepsilon \perp$ is a dielectric constant perpendicular to the molecular axis, with the test conditions being 25±0.50° C., 1 KHz, HP4284A, and 5.2 □m TN left-handed cell.

γ1: is a rotary viscosity, with a unit of mPa·s, with the test conditions being 25±0.5° C.

VHR: is a voltage holding ratio (%), with the test conditions being 20±2° C., a voltage of ±5 V, a pulse width of 10 ms, and a voltage holding time of 16.7 ms. The test equipment is a TOYO Model 6254 liquid crystal performance comprehensive tester.

In the reaction process, the reaction progress is generally monitored by means of TLC, and treatments after the completion of the reaction are generally water washing, extraction, organic phase combination and drying, solvent evaporation under reduced pressure, as well as recrystallization and column chromatography; and a person skilled in the art would be able to implement the present invention according to the following description.

Route 1: $Z_2$ is —OCF$_2$—; reference can be made to "Chemical Reagents", 2015, 37(1), 40-43; 48, "Progress on Synthesis of Liquid Crystalline Compounds Containing Difluoromethyleneoxy-bridged Groups"

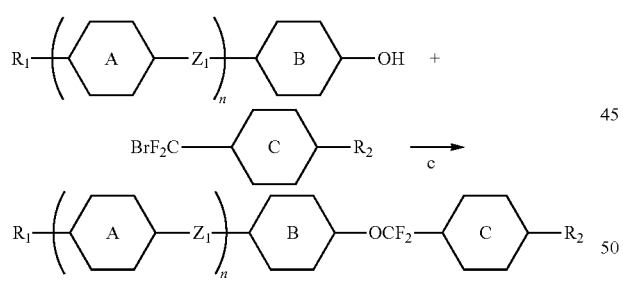

c: DMF anhydrous potassium carbonate

Route 2: $Z_2$ is —CF$_2$O—; reference can be made to "Chemical Reagents", 2015, 37(1), 40-43; 48, "Progress on Synthesis of Liquid Crystalline Compounds Containing Difluoromethyleneoxy-bridged Groups"

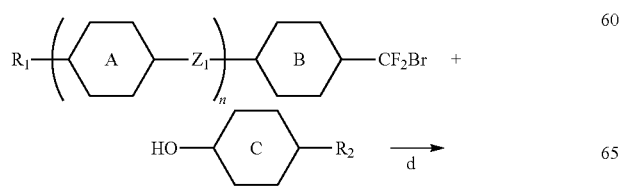

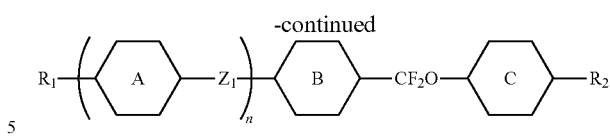

d: DMF anhydrous potassium carbonate

Route 3: $Z_2$ is —CH$_2$O—;

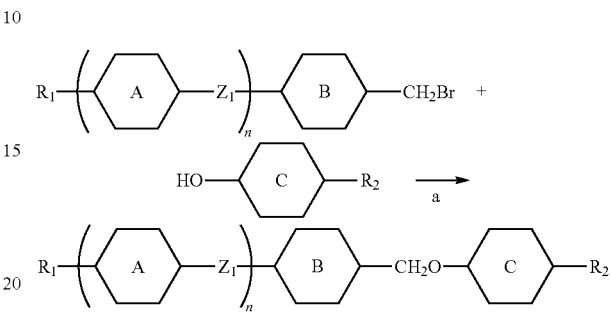

a: DMF K$_2$CO$_3$

Route 4: $Z_2$ is —OCH$_2$—;

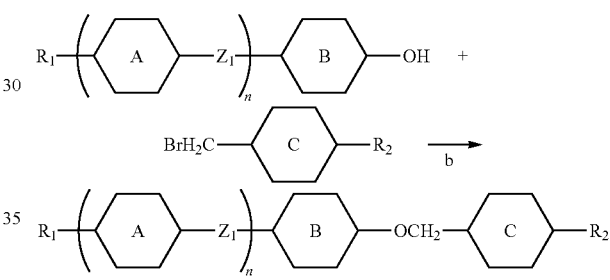

b: DMF K$_2$CO$_3$

In the examples of the present invention application, liquid crystal monomer structures are represented by codes, wherein the code representation of ring structures, end groups and linking groups of the liquid crystals are shown in tables (I) and (II) below

TABLE (I)

| Corresponding code for ring structure | |
|---|---|
| Ring structure | Corresponding code |
| (cyclohexane) | C |
| (cyclohexene) | L |
| (difluorobenzene) | U |

TABLE (I)-continued

Corresponding code for ring structure

| Ring structure | Corresponding code |
|---|---|
|  | P |
| 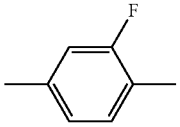 | G |
| 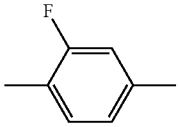 | Gi |
| 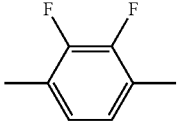 | Y |
| 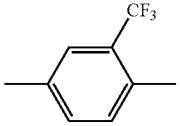 | K |
| 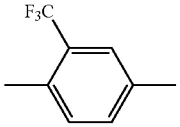 | Ki |
| 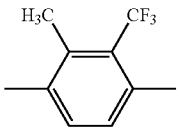 | K(2CH$_3$) |
| 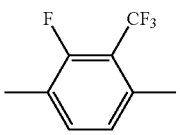 | K(2F) |
| 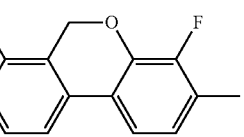 | Sa |
| 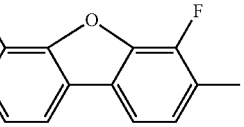 | Sb |
| 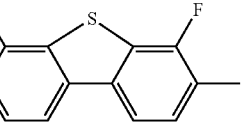 | Sc |

TABLE (II)

Corresponding code for end group and linking group

| End groups and linking groups | Corresponding code |
|---|---|
| $C_nH_{2n+1}$— | n- |
| $C_nH_{2n+1}O$— | nO— |
| —OCF$_3$ | —OT |
| —CF$_2$O— | —Q— |
| —OCF$_2$— | —Qi— |
| —CH$_2$O— | —O— |
| —OCH$_2$— | —Oi— |
| —F | —F |
| —CN | —CN |
| —CH$_2$CH$_2$— | —E— |
| —CH=CH— | —V— |
| —C≡C— | —W— |
| —COO— | —COO— |
| —CH=CH—$C_nH_{2n+1}$ | Vn— |
| 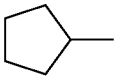 | C(5)- |
|  | C(3)1- |

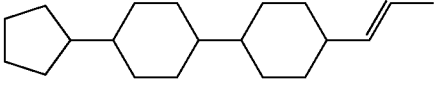

CCV-C(5)-1

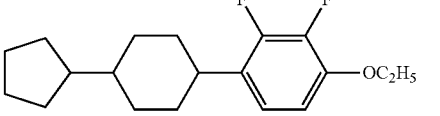

CY-C(5)-02

Example 1

(1-a)

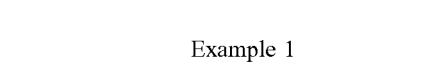

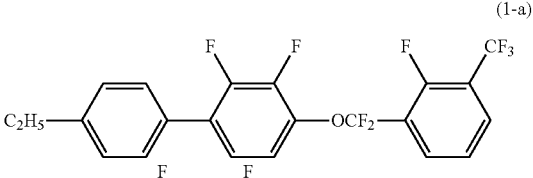 +

(1-a-1)

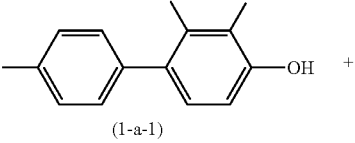 →

(1-a-2)

23.4 g (0.1 mole) of (1-a-1), 35.6.0 g (0.11 mole) of (1-a-2), 200 ml of DMF and 18 g of anhydrous potassium carbonate are charged into a 500 ml three-necked flask, are reacted at 100° C. for 3 hours under stirring, and poured into 1000 nl of water, extraction is carried out using toluene, and the organic phase is washed with water, subjected to evaporation to remove toluene, dissolved in petroleum ether, passes through a silica gel column, and is recrystallized twice by means of toluene+petroleum ether to obtain 19.4 g of product (1-a), with Gc: 99.89%

Δε: −2.1
Δn: 0.081
$\varepsilon_\perp$: 8.9
$\gamma_1$: 43

The sole FIGURE is a mass spectrum of compound (1-a).

With reference to the synthesis method of Example 1, only except that some of the raw materials are replaced, the following compounds can be synthesized Δε: -2.1
Δn: 0.11
$\varepsilon_\perp$: 8.9
$\gamma_1$: 90

Example 2

34.6 g (0.1 mole) of (2-a-1), 23.32.0 g (0.11 mole) of (2-a-2), 200 ml of DMF and 18 g of anhydrous potassium carbonate are charged into a 500 ml three-necked flask, are reacted at 100° C. for 3 hours under stirring, and poured into 1000 nl of water, extraction is carried out using toluene, and the organic phase is washed with water, subjected to evaporation to remove toluene, dissolved in petroleum ether, passes through a silica gel column, and is recrystallized twice by means of toluene+petroleum ether to obtain 20.4 g of product (2-a), with Gc: 99.90%

Δε: -2.3
Δn: 0.09
$\varepsilon_\perp$: 9.0
$\gamma_1$: 46

-continued

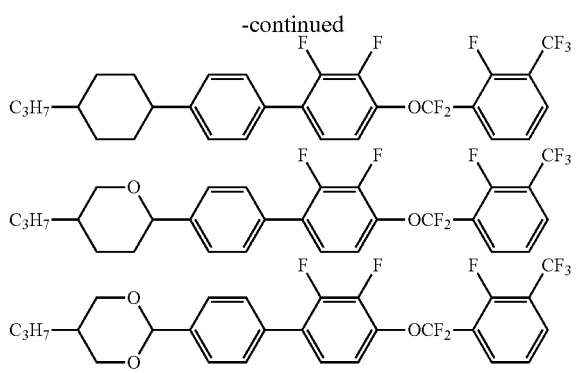

Comparative Compound (AA)

Δε: −0.9
the dielectric anisotropy is positive.

Example 3

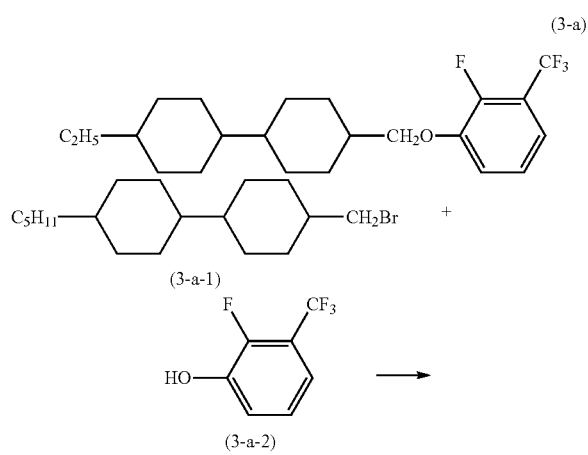

32.8 g (0.1 mole) of (3-a-1), 23.32.0 g (0.11 mole) of (3-a-2), 200 ml of DMF and 18 g of anhydrous potassium carbonate are charged into a 500 ml three-necked flask, are reacted at 80° C. for 5 hours under stirring, and poured into 1000 nl of water, extraction is carried out using petroleum ether, and the organic phase is washed with water, passes through a silica gel column, and is recrystallized 4 times by means of petroleum ether to obtain 27.4 g of product (3-a), with Gc: 99.85%

Δε: −3.3
Δn: 0.08
$\Delta_\perp$: 9.2
$\gamma_1$: 80

Example 4

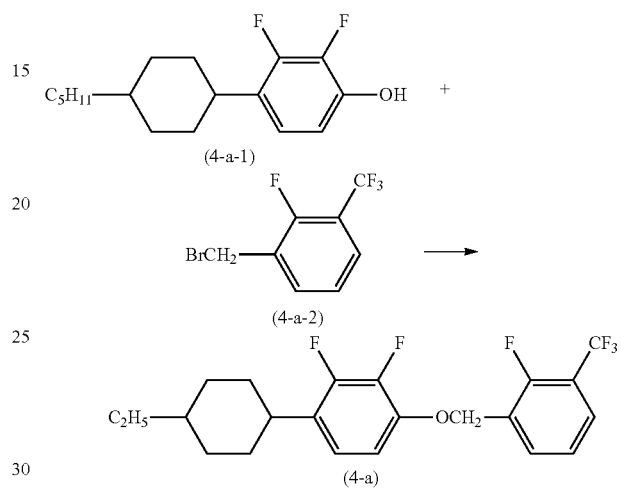

28.2 g (0.1 mole) of (4-a-1), 31.68 g (0.11 mole) of (4-a-2), 200 ml of DMF and 18 g of anhydrous potassium carbonate are charged into a 500 ml three-necked flask, are reacted at 50° C. for 5 hours under stirring, and poured into 1000 nl of water, extraction is carried out using petroleum ether, and the organic phase is washed with water, passes through a silica gel column, and is recrystallized 4 times by means of petroleum ether to obtain 29.4 g of product (4-a), with Gc: 99.88%

Δε: −2.3
Δn: 0.09
$\Delta_\perp$: 8.9
$\gamma_1$: 80

Example 5

Liquid Crystal Composition

| Category | Liquid crystal monomer code | Content (%) |
| --- | --- | --- |
| I | PYQK(2F)-3 | 10 |
| I | PYQiK(2F)-3-O2 | 10 |
| I | PGYQK(2F)-3 | 10 |
| I | APYQK(2F)-2 | 10 |
| II | CC-3-2 | 30 |
| II | CC-3-V | 5 |
| II | CC-3-V1 | 5 |
| II | CCP-3-1 | 7 |
| II | CPP-3-2 | 8 |
| II | CPP-3-2V1 | 5 |

Δε: −1.1
Δn: 0.08
Cp: 50° C.
$\gamma_1$: 35 mPa·s.

After the mixture is stored at −20° C. for 200 hours, no crystal of the compound of formula I is precipitated.

Example 6

Liquid Crystal Composition

| Category | Liquid crystal monomer code | Content (%) |
|---|---|---|
| I | CCQK(2F)-3 | 10 |
| I | PYQiK(2F)-5-O2 | 10 |
| I | PYQKi(3F)-5 | 8 |
| I | CPK(2F)-3 | 2 |
| II | CC-3-2 | 25 |
| II | CC-3-V | 5 |
| II | CPP-1V-2 | 5 |
| II | CPP-3-2V1 | 5 |
| V | PY-3-O2 | 5 |
| V | CPY-3-O2 | 5 |
| V | CCY-3-O2 | 5 |
| V | CY-3-O4 | 5 |
| V | CCOY-3-O2 | 5 |
| V | COY-3-O2 | 2 |
| V | PYP-C(3)1-2 | 2 |
|  | Sb-C(5)O-O4 | 1 |

Δε: −2.4
Δn: 0.09
Cp: 75° C.
$\gamma_1$: 80 mPa · s.

This liquid crystal composition has a moderate Δε, a moderate Δn, a lower $\gamma_1$, and a high Cp, and is suitable for use in liquid crystal materials for rapid response TN, IPS, and FFS-TFT displays.

After the mixture is stored at −20° C. for 200 hours, no crystal of the compound of formula I is precipitated.

Where 10% of the compound of formula I, i.e., PYQiK (2F)-5-O2, is replaced by comparative compound (AA), crystals of compound (AA) are precipitated after the mixture is stored at −20° C. for 100 hours.

A composition formed by adding RM-2 at a concentration in mass percentage of 0.3% of the liquid crystal composition of Example 6 can be applied to PSVA display mode.

Example 7

Liquid Crystal Composition

| Category | Liquid crystal monomer code | Content (%) |
|---|---|---|
| I | PYQiK(2F)-2-O2 | 5 |
| I | CCOK(2F)-3-O2 | 5 |
| I | PGYQKi(3F)-5 | 5 |
| I | APYQK(2F)-5 | 5 |
| II | CC-3-2 | 25 |
| II | CC-3-V | 5 |
| II | PP-1-5 | 5 |
| II | CPP-1V-2 | 5 |
| V | CY-3-O2 | 5 |
| V | CPY-3-O2 | 10 |
| V | CCY-3-O2 | 10 |
| V | CPY-C(3)1-O2 | 5 |
| V | CCOY-3-O2 | 5 |
|  | Sa-C(5)O-O4 | 5 |

Δε: −3.2
Δn: 0.090
Cp: 78° C.
$\gamma_1$: 55 mPa · s.

After the mixture is stored at −20° C. for 200 hours, no crystal of the compound of formula I is precipitated.

Example 8

Liquid Crystal Composition

| Category | Liquid crystal monomer code | Content (%) |
|---|---|---|
| I | PGYQiK(2F)-2 | 3 |
| I | APYQK(2F)-3 | 3 |
| I | PYQK(2F)-5 | 3 |
| II | CC-3-5 | 10 |
| II | PP-1-2V | 5 |
| II | CPP-3-2 | 4 |
| II | CCP-3-O1 | 2 |
| V | CY-3-O2 | 10 |
| V | CPY-3-O2 | 15 |
| V | CCY-3-O2 | 10 |
| V | CPY-C(5)-O2 | 10 |
| V | CCOY-3-O2 | 10 |
| V | COY-C(5)-O2 | 10 |
|  | Sc-C(5)O-O4 | 5 |

Δε: −4.4
Δn: 0.10
Cp: 80° C.
$\gamma_1$: 120 mPa · s.

After the mixture is stored at −20° C. for 200 hours, no crystal of the compound of formula I is precipitated.

Example 9

Dielectrically Positive Liquid Crystal Composition

| Category | Liquid crystal monomer code | Content (%) |
|---|---|---|
| I | PYQK(2F)-3 | 3 |
| I | CCOK(2F)-2 | 2 |
| I | PYPQK-3 | 5 |
| II | CC-3-V | 30 |
| II | CC-2-3 | 5 |
| II | CC-3-V1 | 5 |
| II | PP-2V-1 | 3 |
| II | CCP-3-1 | 2 |
| II | CPP-3-2V1 | 5 |
| III | CCG-3-F | 5 |
| III | CPU-3-F | 5 |
| III | CCP-3-OT | 5 |
| III | PPGI-3-F | 5 |
| IV | PUQU-C(5)-F | 1 |
| IV | PUQU-C(3)1-F | 1 |
| IV | PGUQU-3-F | 1 |
| IV | PGUQU-C(3)1-F | 2 |
| IV | PGUQU-C(5)-F | 2 |
| IV | APUQU-C(5)-F | 3 |

Δε: 6.0
Δn: 0.10
Cp: 60° C.
$\gamma_1$: 40 mPa · s.

After the mixture is stored at −20° C. for 200 hours, no crystal of the compound of formula I is precipitated.

Example 10

Dielectrically Positive Liquid Crystal Composition

| Category | Liquid crystal monomer code | Content (%) |
|---|---|---|
| I | PYQiK(2F)-3 | 5 |
| I | CCOK(2F)-5-O2 | 5 |
| I | PYQK(2F)-3-O2 | 5 |

| Category | Liquid crystal monomer code | Content (%) |
|---|---|---|
| II | CC-3-V | 30 |
| II | CC-5-3 | 5 |
| II | CC-3-V1 | 5 |
| II | CCP-V2-1 | 5 |
| II | CCP-V-1 | 5 |
| II | CPP-1V-2 | 3 |
| III | PGP-C(3)-2 | 5 |
| III | PPGU-C(5)-F | 1 |
| III | CPUP-3-OT | 5 |
| III | PGP-3-F | 5 |
| IV | PUQU-C(5)-F | 8 |
| IV | PUQU-C(3)1-F | 2 |
| IV | PGUQU-3-F | 1 |
| IV | PGUQU-C(3)1-F | 2 |
| IV | PGUQU-C(5)-F | 1 |
| IV | CPUQU-C(5)-F | 1 |
| IV | DUQU-C(5)-F | 1 |

Δε: 4.8
Δn: 0.101
Cp: 75° C.
γ1: 65 mPa · s.

After the mixture is stored at −20° C. for 200 hours, no crystal of the compound of formula I is precipitated.

The liquid crystal compound of formula I has a negative dielectric anisotropy, a good low temperature performance, and a good stability to UV and high temperatures, and has varying Δn, Δε, Cp and γ1 properties depending on R,

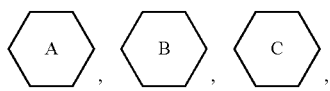

Z, X, m, n and p, and therefore it has a wider range of applications, and can be used for formulating various positive and negative liquid crystal mixtures with different parameters.

The invention claimed is:

1. A liquid crystal compound, represented by formula 2-a, 1-b to 1-e, 3-a or 4-a:

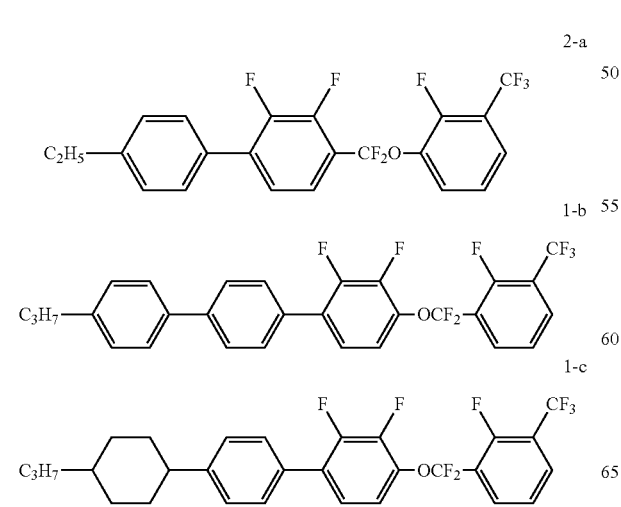

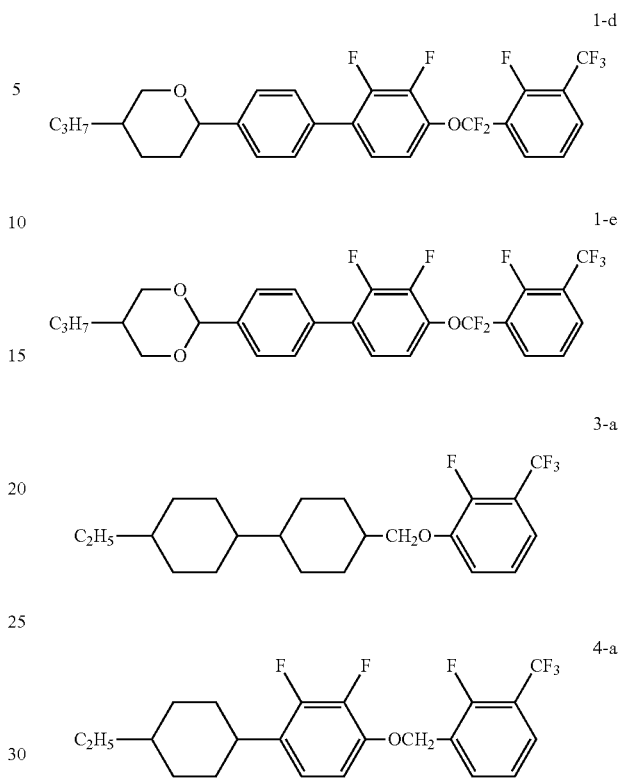

2. A liquid crystal mixture, comprising one or more compounds represented by formula 2-a, 1-b to 1-e, 3-a and 4-a of claim 1, and one or more compounds represented by formula II

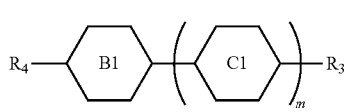

wherein $R_3$ and $R_4$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

m represents 1 or 2; and

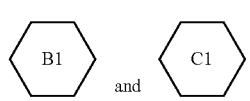

each independently represent one or more of phenylene, cyclohexylene and/or cyclohexenylene.

3. The liquid crystal mixture according to claim 2, wherein concentrations in mass percentage of said compound represented by formula 2-a, 1-b to 1-e, 3-a and 4-a and said compound represented by formula II are respectively 1-40% and 1-65%.

4. The liquid crystal mixture according to claim 2, wherein said one or more compounds represented by formula II are one or more of compounds represented by formulas II1 to II22 below:
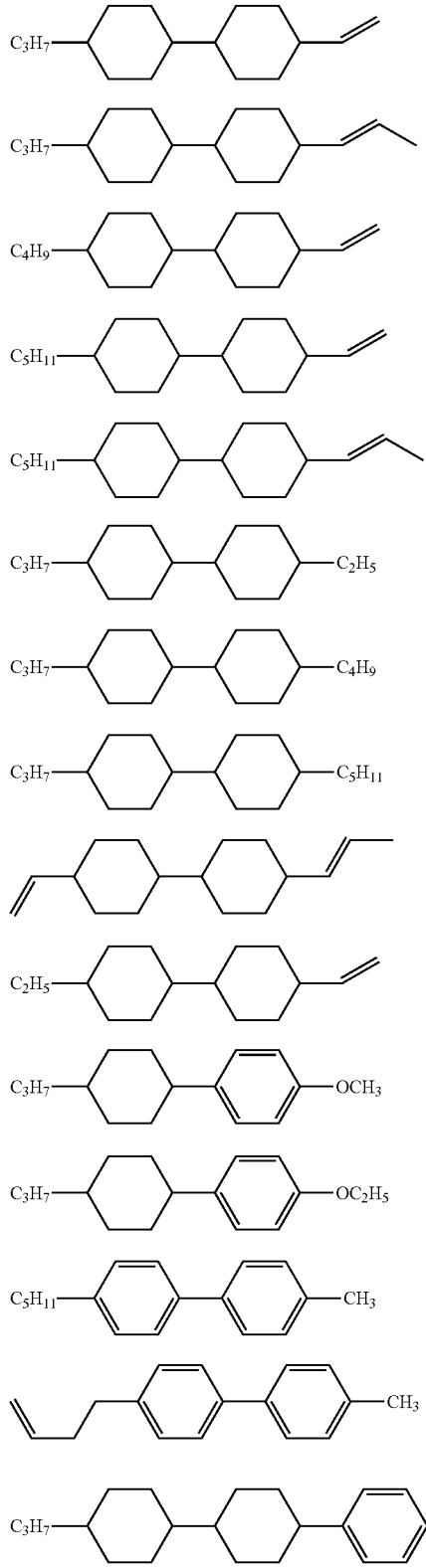
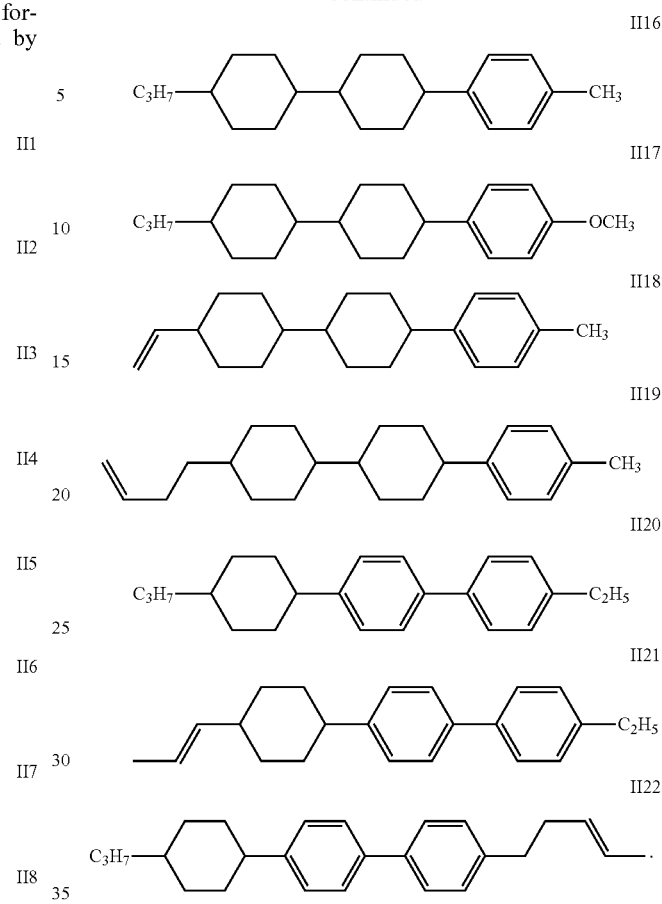
5. The liquid crystal mixture according to claim 2, wherein said liquid crystal mixture further comprises one or more of compounds represented by formulas III1 to III14 below:
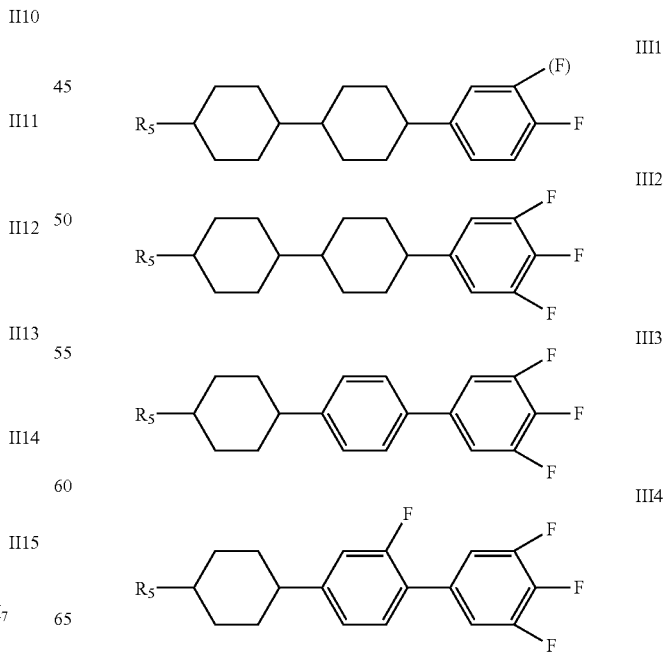

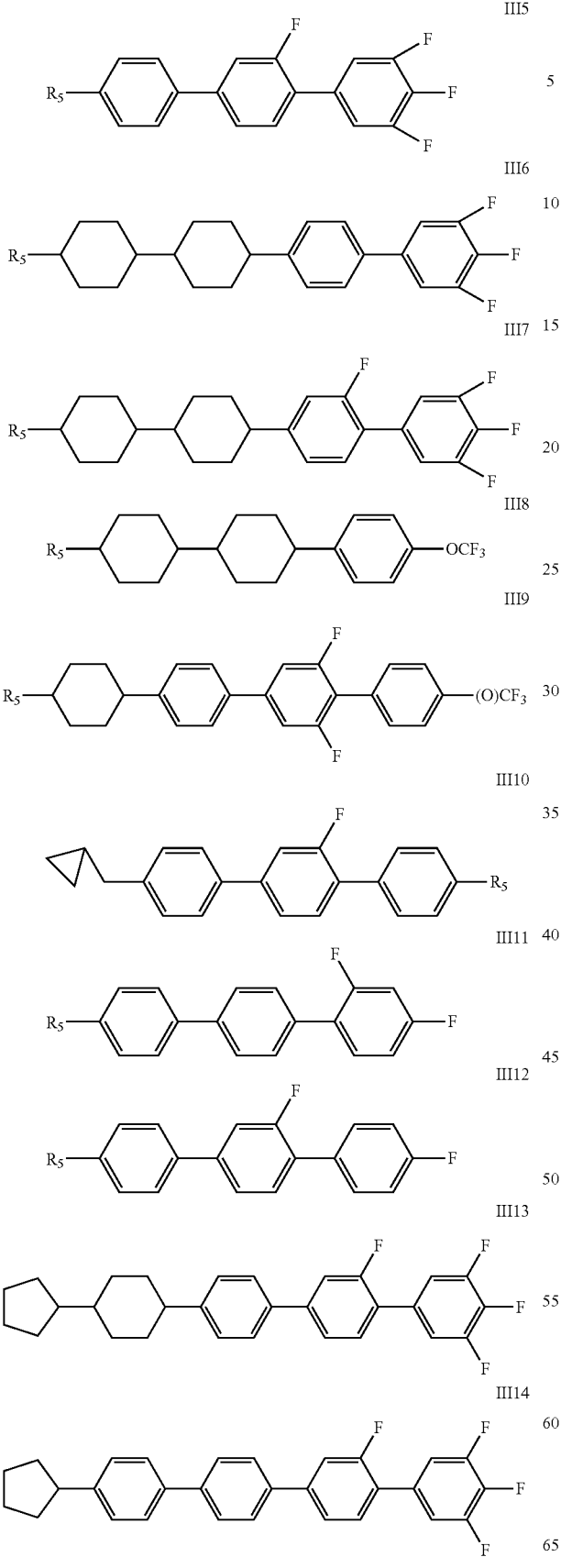

wherein each $R_5$ independently represents H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

(F) represents F or H; and (O) represents O or a single bond.

6. The liquid crystal mixture according to claim 2, wherein said liquid crystal mixture further comprises one or more compounds represented by formula IV:

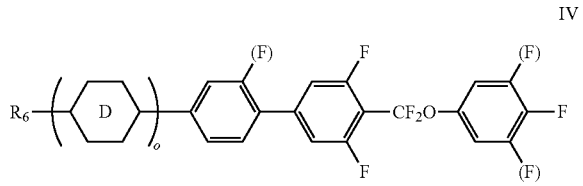

IV wherein $R_6$ represents H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

o represents 0 or 1;

each (F) independently represents H or F; and

represents phenylene, cyclohexylene, cyclohexenylene, or a group formed by substituting one or two non-connected $CH_2$ in cyclohexylene with O.

7. The liquid crystal mixture according to claim 2, wherein the liquid crystal mixture may further comprise one or more negative compounds of formula V,

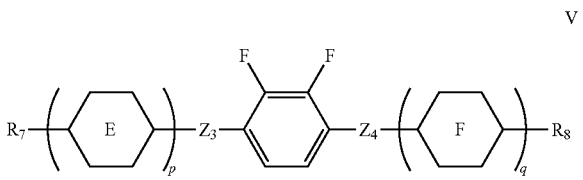

V wherein $R_7$ and $R_8$ each independently represent H, an alkyl group having a carbon atom number of 1-5, an alkenyl group having a carbon atom number of 2-6, or an alkoxy group having a carbon atom number of 1-5, wherein any $CH_2$ therein may be substituted with cyclopentyl, cyclobutyl or cyclopropyl;

p and q each independently represent 0, 1 or 2, with $1 \leq p+q \leq 3$;

$Z_3$ and $Z_4$ each independently represent a single bond, —$CH_2CH_2$—, —$CH_2O$—, —$OCH_2$— or —$CF_2O$—; and

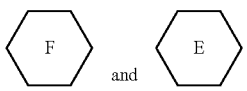

each independently represent one or more of

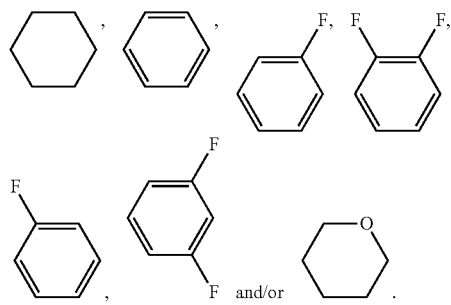

8. The liquid crystal mixture according to claim 2, wherein said liquid crystal mixture further comprises one or more compounds represented by formula VI:

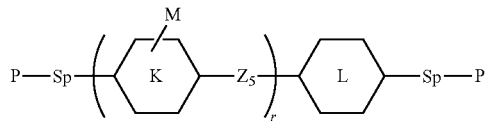

VI wherein each P independently represents a polymerizable functional group;

each Sp independently represents a spacer group;

M represents H, -Sp-P, F, an alkyl group having a carbon atom number of 1-5, an alkoxy group having a carbon atom number of 1-5, or an alkenyl group having a carbon atom number of 2-5;

r represents 0, 1 or 2;

$Z_5$ represents a single bond, —COO—, —C≡C—, —C=C— or —CH$_2$O—; and

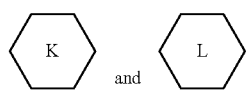

each independently represent one or more of a benzene ring, cyclohexane, indane or a naphthalene ring.

9. A liquid crystal display element or liquid crystal display comprising the liquid crystal compound or mixture of claim 1, wherein said display element or display is an active matrix display element or display or a passive matrix display element or display.

* * * * *